US012753358B2

(12) United States Patent
Velazquez et al.

(10) Patent No.: US 12,753,358 B2
(45) Date of Patent: Oct. 6, 2026

(54) PROCESS FOR OBTAINING ALKYLATION GASOLINE THROUGH THE USE OF REFINERY BLENDS AND ORGANIC ACIDS

(71) Applicant: Instituto Mexicano del Petróleo, Mexico City (MX)

(72) Inventors: Heriberto Diaz Velazquez, Mexico City (MX); Rafael Martinez Palou, Mexico City (MX); José Gonzalo Hernández Cortez, Mexico City (MX); Jazmin Narcedalia Castillo Cervantes, Mexico City (MX); Javier Guzmán Pantoja, Mexico City (MX)

(73) Assignee: Instituto Mexicano del Petróleo, Mexico City (MX)

( * ) Notice: Subject to any disclaimer, the term of this patent is extended or adjusted under 35 U.S.C. 154(b) by 232 days.

(21) Appl. No.: 18/781,030

(22) Filed: Jul. 23, 2024

(65) Prior Publication Data

US 2025/0043201 A1 Feb. 6, 2025

(30) Foreign Application Priority Data

Jul. 31, 2023 (MX) .................... MX/a/2023/009023

(51) Int. Cl.
*C10L 1/06* (2006.01)
*C07C 2/64* (2006.01)
*C07C 2/70* (2006.01)

(52) U.S. Cl.
CPC *C10L 1/06* (2013.01); *C07C 2/64* (2013.01); *C07C 2/70* (2013.01);

(Continued)

(58) Field of Classification Search
CPC ............... C10L 1/06; C10L 2200/0423; C10L 2290/06; C10L 2290/12; C10L 2290/141;

(Continued)

(56) References Cited

U.S. PATENT DOCUMENTS 5,220,095 A 6/1993 Hommeltoft
5,284,993 A * 2/1994 Eastman .............. B01J 31/0225 585/723

(Continued)

OTHER PUBLICATIONS

Tian, Ying, et al. "A novel application of methanesulfonic acid as catalyst for the alkylation of olefins with aromatics." Industrial & engineering chemistry research 51.42 (2012): 13627-13631.

(Continued)

*Primary Examiner* — Ali Z Fadhel
(74) *Attorney, Agent, or Firm* — FisherBroyles, LLP; Jason P. Mueller

(57) ABSTRACT

The present disclosure describes a new production process of alkylate gasoline through the application of a Batch reactor which mixes a hydrocarbon feed from an alkylation plant containing olefins and iso-paraffins, and methanesulfonic acid as the catalyst, under certain conditions of pressure, and temperature, at weight ratio no lower than 50 weight % of catalyst respective to hydrocarbons, and a stirring velocity of 1000 rpm. The alkylate product keeps a quality similar to that obtained using commercial catalysts such as sulfuric acid. The new catalyst can be reused up to 4 reaction cycles without significant reduction in its catalytic activity.

5 Claims, 9 Drawing Sheets

(52) U.S. Cl.
CPC ... *C10L 2200/0423* (2013.01); *C10L 2290/06* (2013.01); *C10L 2290/12* (2013.01); *C10L 2290/141* (2013.01); *C10L 2290/44* (2013.01)

(58) Field of Classification Search
CPC ......... C10L 2290/44; C07C 2/64; C07C 2/70; C10G 2400/02
See application file for complete search history.

(56) References Cited

U.S. PATENT DOCUMENTS

| | | | | |
|---|---|---|---|---|
| 5,292,986 | A | 3/1994 | Abbott | |
| 5,347,065 | A | 9/1994 | Anderson | |
| 2022/0410134 | A1 * | 12/2022 | Shiflett | B01J 31/0277 |

OTHER PUBLICATIONS

BP Energy Outlook 2023 Edition, Jul. 2023, 66 pages.
Chapter 10: Alkylation, Fundamentals of Petroleum Refining, 2010 Elsevier BV, 21 pages.
Zhao, Zhongkui, et al. "An efficient method for the alkylation of α-methylnaphthalene with various alkylating agents using methanesulfonic acid as novel catalysts and solvents." Catalysis letters 102 (2005): 219-222.
Wu, Xiaolin, et al. "Gasoline Desulfurization by catalytic alkylation over methanesulfonic acid." Bulletin of the Korean Chemical Society 34.10 (2013): 3055-3058.
Balasubramanian, Sujithra, and Ponnusami Venkatachalam. "Green synthesis of carbon solid acid catalysts using methane sulfonic acid and its application in the conversion of cellulose to platform chemicals." Cellulose 29.3 (2022): 1509-1526.
Leleti, Rajender Reddy, et al. "Highly selective methanesulfonic acid-catalyzed 1, 3-isomerization of allylic alcohols." Tetrahedron Letters 48.48 (2007): 8505-8507.
Singhal, Shailey, et al. "Ionic liquids: Green catalysts for alkene-isoalkane alkylation." Journal of Molecular Liquids 285 (2019): 299-313.
Zhang, Tong, Xu Li, and Jinxiang Dong. "Methanesulfonic acid as a more efficient catalyst for the synthesis of lauraldehyde glycerol acetal." Tenside Surfactants Detergents 51.6 (2014): 516-520.
Luong, B. X., et al. "Use of methanesulfonic acid as catalyst for the production of linear alkylbenzenes." Journal of catalysis 226.2 (2004): 301-307.
Díaz Velázquez, Heriberto, et al. "New insights into the progress on the isobutane/butene alkylation reaction and related processes for high-quality fuel production. A critical review." Energy & Fuels 34.12 (2020): 15525-15556.
Velázquez, Heriberto Díaz, et al. "Recent progress on catalyst technologies for high quality gasoline production." Catalysis Reviews 65.4 (2023): 1079-1299.
Gan, Panxue, and Shengwei Tang. "Research progress in ionic liquids catalyzed isobutane/butene alkylation." Chinese journal of chemical engineering 24.11 (2016): 1497-1504.
Kore, Rajkumar, Aaron M. Scurto, and Mark B. Shiflett. "Review of isobutane alkylation technology using ionic liquid-based catalysts—where do we stand?." Industrial & Engineering Chemistry Research 59.36 (2020): 15811-15838.
Góra, Maciej, et al. "Solvent-free condensations of ketones with malononitrile catalysed by methanesulfonic acid/morpholine system." Green Chemistry 11.6 (2009): 863-867.
Campisciano, Vincenzo, Francesco Giacalone, and Michelangelo Gruttadauria. "Supported ionic liquids: a versatile and useful class of materials." The Chemical Record 17.10 (2017): 918-938.
Weitkamp, Jens, and Yvonne Traa. "Isobutane/butene alkylation on solid catalysts. Where do we stand?." Catalysis Today 49.1-3 (1999): 193-199.
Chang, Qiong, et al. "Methylsulfonic Acid Adsorbed on Silica Gel as a Solid Acid for Dimerization of Indoles: A Convenient Synthesis of 2, 3'-Bi (3 H-indol)-3-one Oximes." Synthetic Communications 43.21 (2013): 2926-2935.

* cited by examiner

PROCESS FOR OBTAINING ALKYLATION GASOLINE THROUGH THE USE OF REFINERY BLENDS AND ORGANIC ACIDS

CROSS-REFERENCE TO RELATED APPLICATIONS

This patent application claims priority under 35 U.S.C. Section 119 to Mexican Patent Application No. MX/a/2023/009023, filed Jul. 31, 2023, the entire disclosure of which is incorporated herein by reference.

FIELD

The object of the present disclosure is to provide a process for producing alkylation gasoline using a batch-type reactor, real hydrocarbon batches, and methane sulfonic acid as the main catalytic medium at optimized conditions of pressure, temperature, and time.

BACKGROUND

The application of petroleum refining operations for the production of high-octane gasoline free of sulfur, olefins, and aromatics will continue to be in high demand for at least the next 30 years, where international policies on greenhouse gas mitigation will allow for the advent of new technologies for vehicle electrification.[1] In the meantime, it is a high priority to ensure the production of high-quality fuels by, for example, improving existing processes, such as the isobutane/butene alkylation process, which has been present in many refineries worldwide since the 1930s.[1,2] The isobutane/butene alkylation process was established as an auxiliary process for the production of aviation fuels, where sulfuric acid ($H_2SO_4$) and hydrofluoric acid (HF) were used as the catalysts par excellence.[3] Today, such acid catalysts are still used in almost all alkylation plants worldwide, except in recent developments such as alkyclean (ABB Lummus), Lurgi Eurofuel, or Alkylene (UOP) or FBA (Haldor-Topsoe).[2,3] It is in the latter development where an organic acid, trifluoromethanesulfonic acid (TFA), supported on silica, is used. Methanesulfonic acid (MSA), although a much less strong acid than TFA, is catalytically active in many organic transformations such as acylation, esterification, condensation, as well as alkylation of aromatic compounds, in cyclization and isomerization reactions.[4,5] Moreover, MSA is considered a green catalyst due to its biodegradable nature, producing $CO_2$ and sulfates as decomposition products.[6-11] Similarly, MSA is much less corrosive and toxic in nature than many organic acids (LD50 in rats 650 mg/kg). Compared to TFA, MSA is very easy to handle and to separate in liquid form. In the present disclosure the use of methanesulfonic acid as a catalyst in isobutane/butene alkylation reactions is reported.

Ionic liquids (ILs) have already been tested on multiple occasions as alkylation catalysts. Most ILs are salts with a halometalate base anion as a Lewis acid source.[4,12-15] Such halometalates, mostly aluminum (haloaluminates), have shown interesting catalytic activity and selectivity towards C8s in isobutane/butene alkylation reactions. However, they suffer from poor chemical stability due to anion hydrolysis reactions. This is why the chemical industry is searching for more stable catalysts that do not contain aluminum salts.

Provided below are references of documents of the state of the art related to the use of MSA as a catalyst in alkylation reactions.

U.S. Pat. No. 5,284,993 by Alan D., Eastman with publication date Feb. 8, 1994, describes a process for removing acid soluble oils, produced as an undesirable byproduct of an acid-catalyzed alkylation reaction, from a mixture containing a strong acid and methanesulfonic acid. The process includes using water to induce the formation of the two immiscible liquid phases of acid soluble oil (ASO) and MSA with water. The two immiscible phases can subsequently be separated from each other.[16] It should be noted that the use of MSA as the sole catalyst in the Isoparaffin/Olefin alkylation process is not mentioned.

U.S. Pat. No. 5,292,986 by Ronald G. Abbott with publication date Mar. 8, 1994, relates to an alkylation catalyst used in processes for alkylating olefin hydrocarbons with isoparaffin hydrocarbons to produce high octane alkylate products suitable for use as a gasoline engine fuel blending component. The new catalyst comprises a mixture of a Lewis acid, a strong Bronsted acid and a predominant amount of a weaker acid. The new alkylation catalyst is used in a new process for alkylating olefinic hydrocarbons with isoparaffinic hydrocarbons. Specifically, the new catalyst comprises antimony pentafluoride, TMA and a predominant amount of MSA.[17] This paper also does not suggest using MSA as the sole catalyst in the Isoparaffin/Olefin Alkylation process.

Similarly, identified below are technical papers in which the central theme only concerns the removal of olefins in aromatics via alkylation employing MSA as a catalyst: 1) "Gasoline Desulfurization by Catalytic Alkylation over Methanesulfonic Acid", Xiaolin Wu; Yunpeng Bai; Ying Tian; Xuan Meng; Li Shi (2013);[18] 2) "A Novel Application of Methanesulfonic Acid as Catalyst for the Alkylation of Olefins with Aromatics", Ying Tian; Xuan Meng; Ji-yun Duan; Li Shi (2012);[19] 3) "An efficient method for the alkylation of α-methylnaphthalene with various alkylating agents using methanesulfonic acid as novel catalyst and sovlents", Zhongkui Zhao; Zongshi Li; Weihong Qiao; Guiru Wang; Lubo Cheng (2005);[20] and, 4) "Use of methanesulfonic acid as a catalyst for the production of linear alkylbenzenes", B. X Luong, A. L Petre, W. F Hoelderich, A Commarieu, J.-A Laffitte, M Espeillac, J.-C Souchet (2004), 18-21.[21]

The present disclosure is directed to overcoming these and other deficiencies in the art.

SUMMARY

The present disclosure describes a new process of production of high-octane gasoline by mixing hydrocarbons coming from a refining plant containing olefins and isoparaffins with an organic acid (MSA), under variable conditions of pressure between 2 and 6 MPa, temperature, between 0 and 140° C., and time, from 5 to 30 min and the fixed conditions of minimum catalyst/hydrocarbon ratio of 50 wt % at 1500 rpm minimum of propellant agitation.

Therefore, one of the objects of the present disclosure is to provide a new process for the production of high-octane gasoline by blending hydrocarbons coming from a refining plant, which contains a mixture of olefins and kerosenes, among which are the precursor molecules of alkylation gasoline.

A further object of the present disclosure is to provide the use of MSA as a single catalyst in an alkylation process with high yields, which are comparable to those obtained by sulfuric acid, applied under its own reaction conditions.

BRIEF DESCRIPTION OF THE DRAWINGS

With the aim clarify the description of the process for the production of alkylate gasoline, through the use of refinery mixtures and organic acids, subject of this disclosure, reference to the drawing will be made, with no limitation of the scope of the present disclosure.

1. Feed tank
2. Micrometric Valve
3. Filter
4. Feeding Bomb
5. Passage Valve
6. Relief Valve
7. Nitrogen Tank
8. Stirring Device
9. Reactor
10. Safety Valve
11. Vent
12. Reaction Mixture
13. Catalyst

DETAILED DESCRIPTION

The present disclosure describes a new process to produce alkylation gasoline by using a batch reactor in which a hydrocarbon load from an alkylation plant composed of olefins and iso-paraffins, and methanesulfonic acid used as catalyst. Hydrocarbons and catalyst are mixed under certain conditions of pressure, time, and temperature, at a weight ratio equal to or less than 50% catalyst to hydrocarbons, and with a stirring of not less than 1500 rpm. The alkylated product maintains the quality to that obtained with commercial catalysts such as sulfuric acid. The new catalyst can be reused without any pretreatment for up to 4 reaction cycles without showing a significant decrease in its catalytic activity.

With the use of hydrocarbon mixtures from a refinery, it is possible to convert iso-paraffins and alkenes into alkylation gasoline (alkylated product), using batch reactors and organic catalysts, such as methanesulfonic acid. The components of the reaction mixture to be transformed are listed in Table 1. This mixture corresponds to the typical feed composition of a hydrofluoric acid-based alkylation plant working in a local refinery in the central region of Mexico, under the operating standards of the state oil company (PEMEX).

Figure 1:
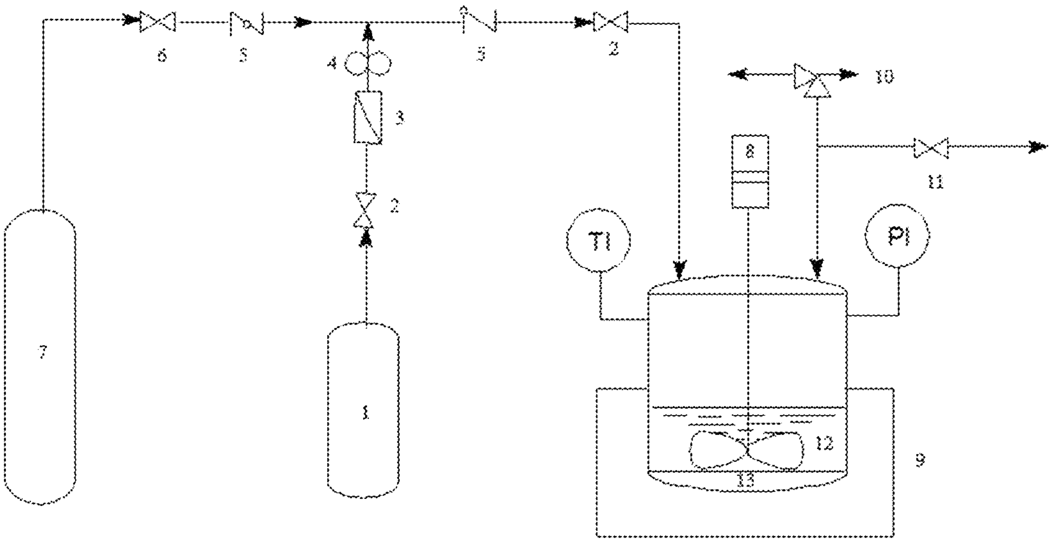
FIG. 1 shows the scheme of the catalyst system used for the alkylation reactions, which contains.

The tests are carried out in a reaction apparatus as shown in FIG. 1, where the batch reactor (9) used is provided with temperature controls and propeller-type stirring means. Externally, the reaction system includes a storage tank for gas loading (1), a tank for the nitrogen feed (7), a tank for the feed (8), discharge and feed valves, among the rest of the peripherals and controls.

TABLE 1

Composition of the gas charge used in alkylation tests.

| Compound | Composition (mol %) |
|---|---|
| Hydrogen | 0.094 |
| C6+/C5= | 0.008 |
| Propane | 0.300 |
| Propylene | 0.794 |
| Isobutane | 67.174 |
| n-Butane | 3.713 |
| 1-Butene | 4.955 |
| Isobutylene | 1.620 |
| t-2-Butene | 5.424 |
| c-2-Butene | 3.518 |
| 1,3-Butadiene | 0.040 |
| Isopentane | 0.011 |
| Carbon Dioxide | 0.003 |
| Etane | 0.004 |
| Oxygen/Argon | 0.114 |
| Nitrogen | 12.228 |
| Total | 100 |

Before the hydrocarbon mixture is loaded into the reactor, the catalyst, which consists only of reagent grade methanesulphonic acid (99% purity), and without prior purification treatment, is added into a Teflon-lined reactor (a mass equivalent to 50% by weight of the hydrocarbon mixture), closing the reactor, and then vacuum is applied to the reactor using a vacuum pump.

After loading the catalyst, the reactor is pre-weighed and the weight is tared on a balance, after which the hydrocarbon mixture (50 weight % of the catalyst) is loaded at −5° C., using micrometric valves to control the flow. Once the reactor is loaded, it is connected to the heating grid, at a rate of 5° C./min until the desired temperature is reached. Once the working temperature (20 to 140° C.) is reached, nitrogen is injected into the reactor to achieve the working pressure. The system pressure (2 to 6 MPa) will tend to vary as the gasoline is formed.

After the reaction time has elapsed, the reactor is cooled down to room temperature to collect gas samples and then, to −5° C., the reactor is completely discharged and collected the liquid product, which is separated by decanting and neutralized with a saturated sodium bicarbonate solution. Both gaseous and liquid samples are taken for gas chromatographic analysis.

Figure 2:
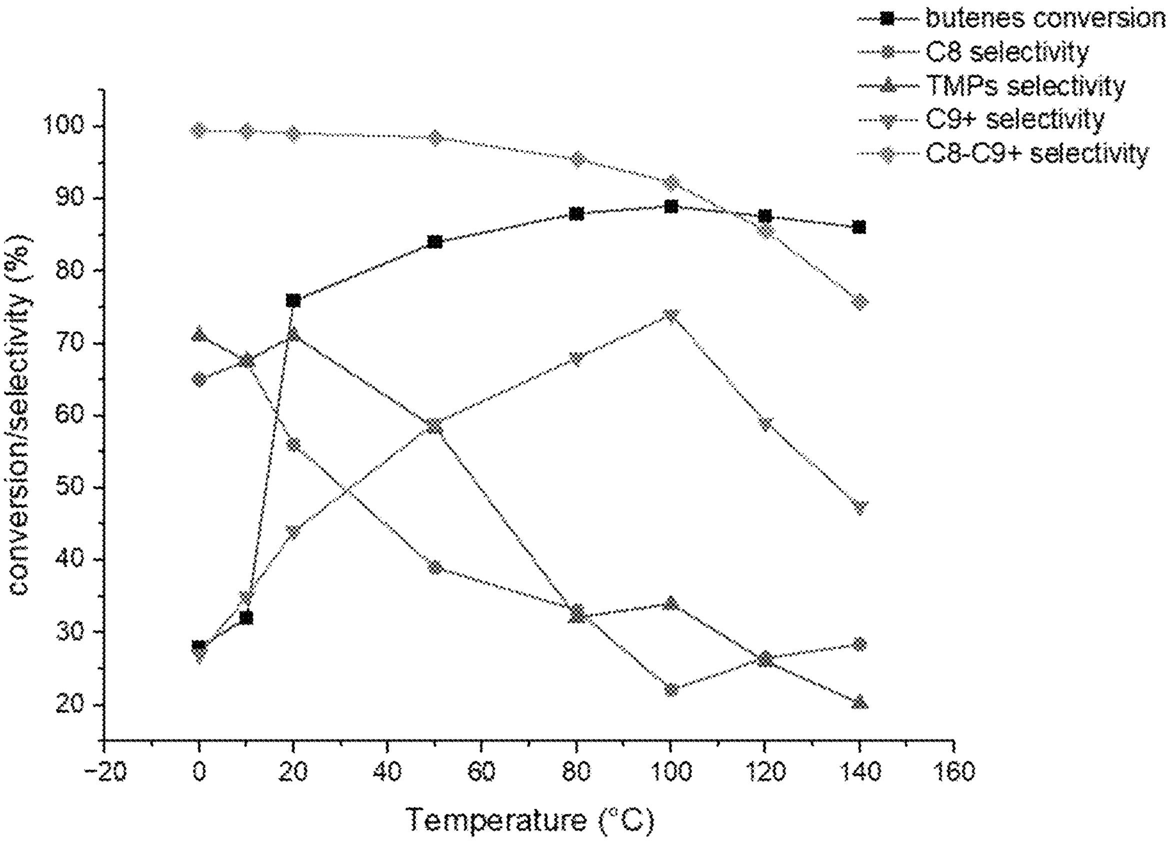
FIG. 2 depicts the plot exhibiting the temperature effect in the alkylate volume and on the TMP/DMH ratio.

Experimental results. Preliminary experiments were carried out to determine the optimal conditions that allow to obtain high olefin conversions, with high C8 content, specially to trimethyl-pentanes (TMPs), which is demonstrated with the values of trimethylpentanes/dimethyl hexanes ratio (TMP/DMH) and the alkylate obtained alkylate volume. Therefore, 3 variables were chosen as the reaction's critical conditions to study, to name: pressure, temperature and reaction time. The interpretation of the results is described as follows:

Effect of the reaction temperature: FIG. 2 exhibits the conversion and selectivity results of the executed tests withing the temperature range of 0 to 140° C. using MSA as catalyst and the following constant conditions: pressure: 2 MPa, time, 30 min, HC/MSA 50 wright %, agitation: 1500 rpm. As FIG. 2 shows, the olefins conversion increases as the temperature does, which provokes an important reactant consumption, leading to an increase in yield and thus, higher gasoline production. In the same FIG. 2, it is also noticeable that the TMPs selectivity drastically decreases because of the increased number of secondary reactions that take place during the process. Such reactions are mainly olefin oligomerization, catalytic cracking of the produced hydrocarbons, or isomerization of some of the hydrocarbon products. Despite this, it is possible to determine that, at high temperatures, it is possible to obtain selectivity values comparable to those that are currently reached using sulfuric acid as catalyst.

Figure 3:
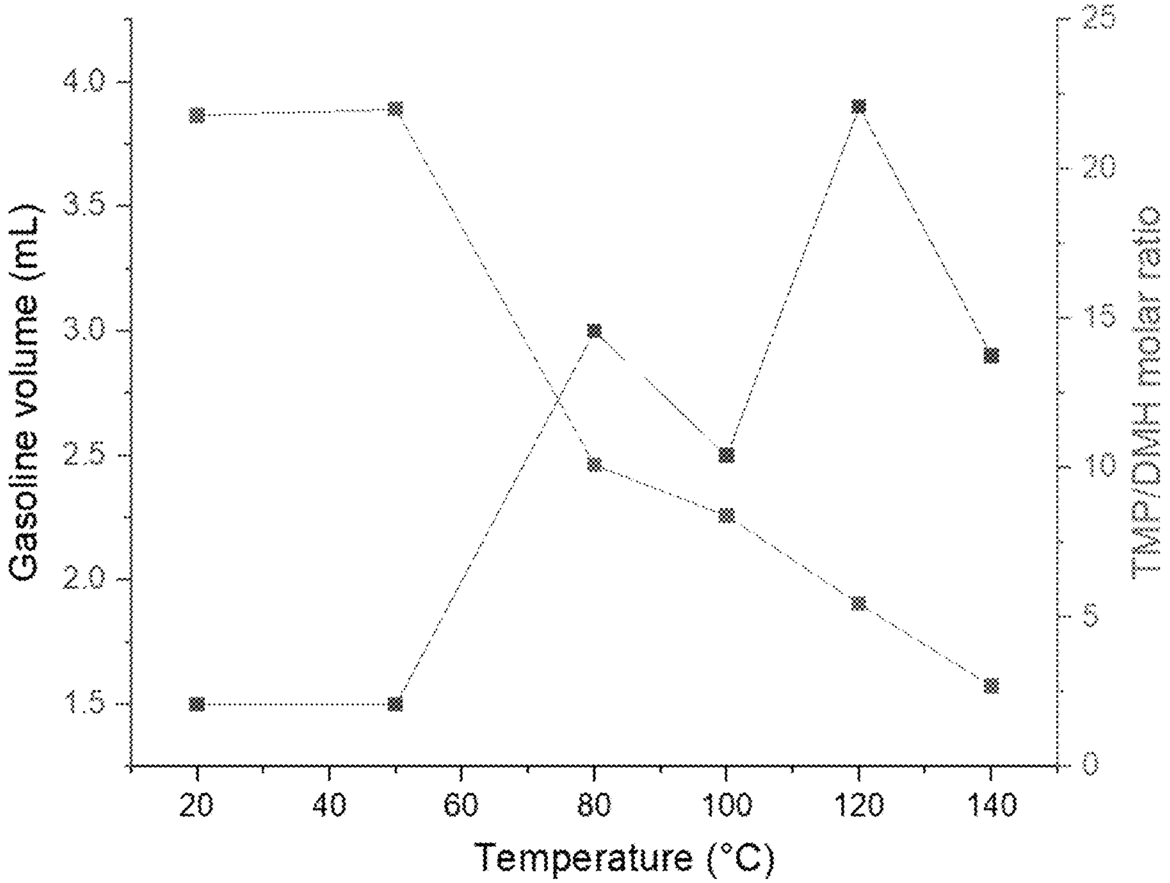
FIG. 3 shows the plot of the effect of the temperature on the olefin's conversion and the selectivity towards the TMPs and C8s hydrocarbons.

FIG. 3 represents the temperature to alkylate volume relationship and the TMP/DMH ratio. This last value is also a significant reference to determine the quality of the alkylate, since sulfuric acid displays a ratio of 6. The results show that, when increasing the reaction temperature, the volume of alkylate gets increased, and the highest volume is reached at 120° C.; however, the quality of the hydrocarbon notoriously decreases. On the other hand, at 80° C. a high gasoline volume is obtained, (about 3.0 mL respective to the amounts of reactants), with the TMP/DMH of about 8.4, higher than that reached by sulfuric acid (TMP/DMH of 6).

Figure 4:
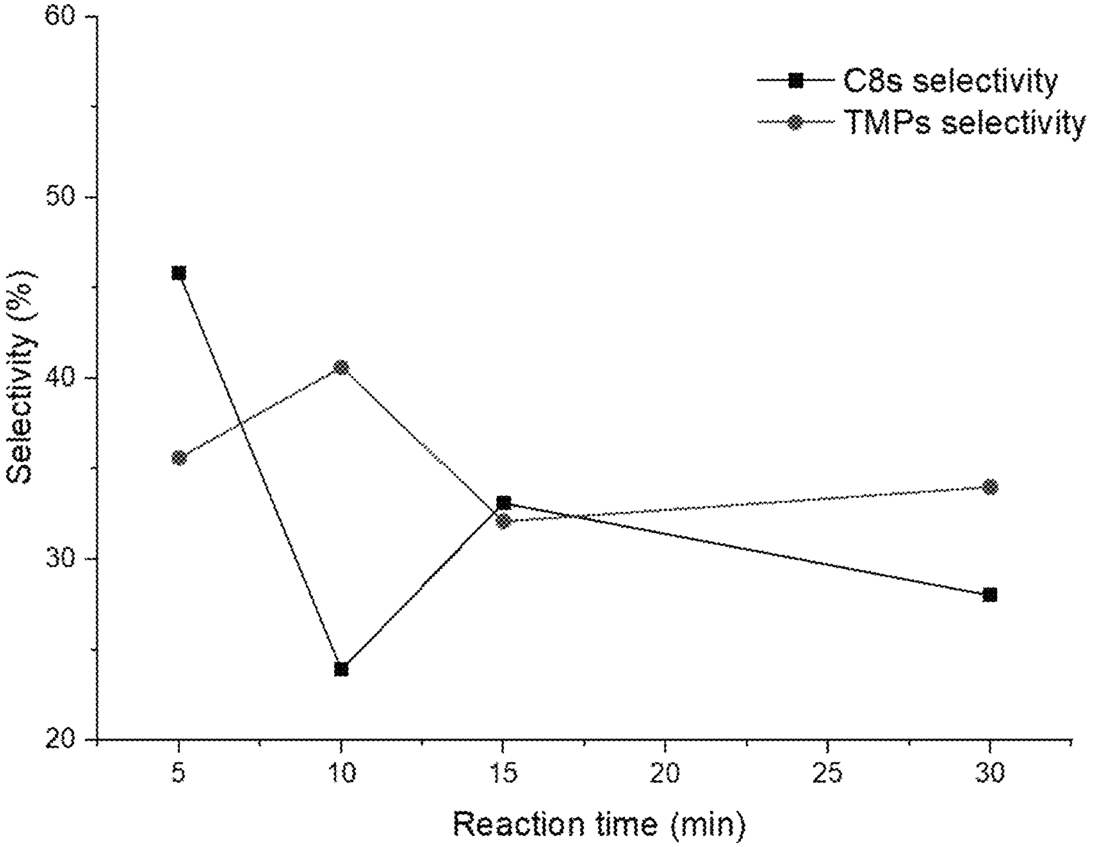
FIG. 4 is the plot showing the effect of reaction time on the selectivity, both to C8s and TMP/DMH.
Figure 5:
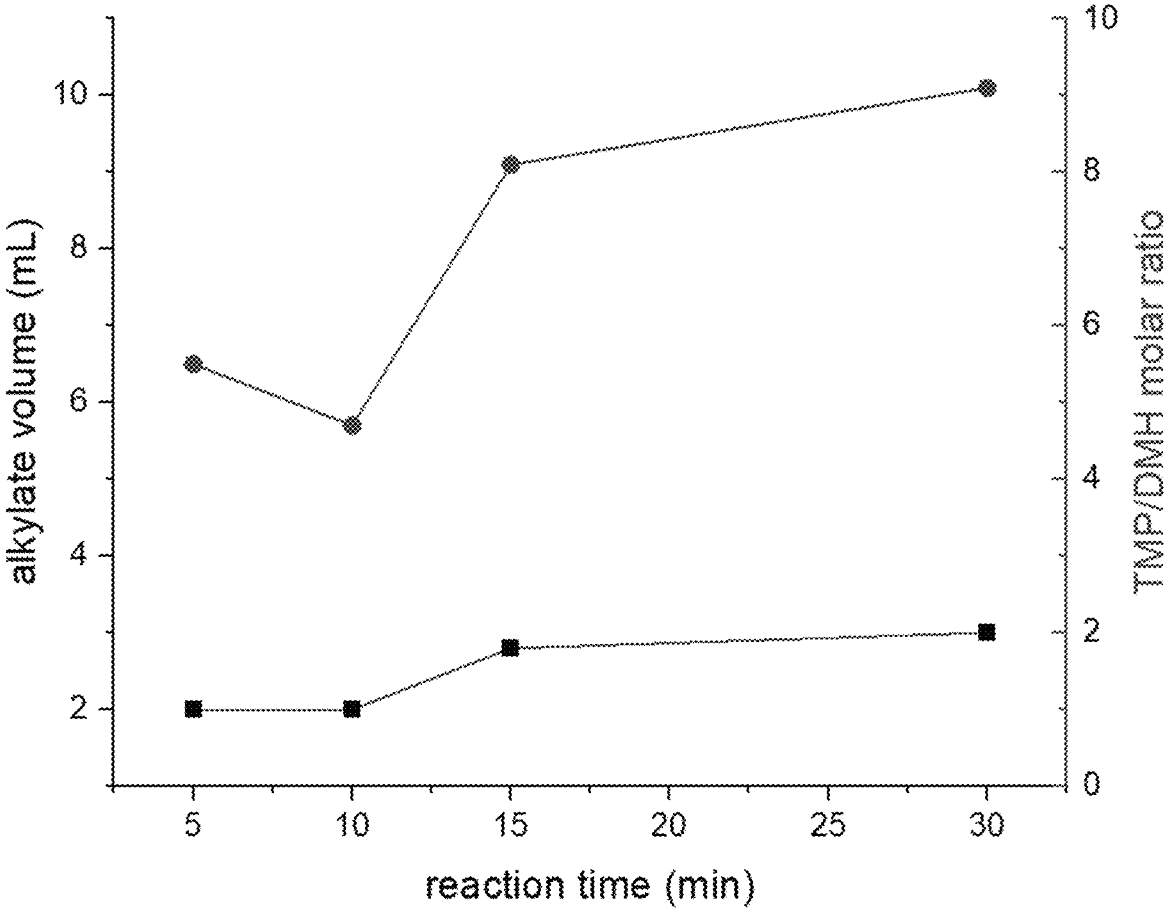
FIG. 5 presents the plot showing the effect of reaction time on the volume of gasoline and on the TMP/DMH ratio.

Effect of the reaction time. The reaction time exerts a significant effect on the gasoline quality that is obtained using the proposed process, this is due to the velocity at which the secondary reactions take place, producing undesired products. These tests were carried out under the following conditions: temperature 80° C., pressure 2 MPa, HC/MSA ratio 50 weight %, agitation: 1500 rpm at 4 different times (5, 10, 15 and 30 min). The results are shown in FIGS. 4 and 5. FIG. 4 shows the relationship between reaction time with the selectivity, from where it can be seen that, at 15 min reaction, the selectivity is drastically decreased. From both figures, it is possible to conclude that high quality gasoline can be obtained at reaction times lower than 30 min. FIG. 5 is a double axe plot, where the relationship between the reaction time and the alkylate volume and TMP/DMH ratio is seen. It is possible to see that at 15 min, one can secure the production of high volumes of gasoline (about 3 mL) of high quality (TMP/DMH ratio of 9.1).

Figure 6:
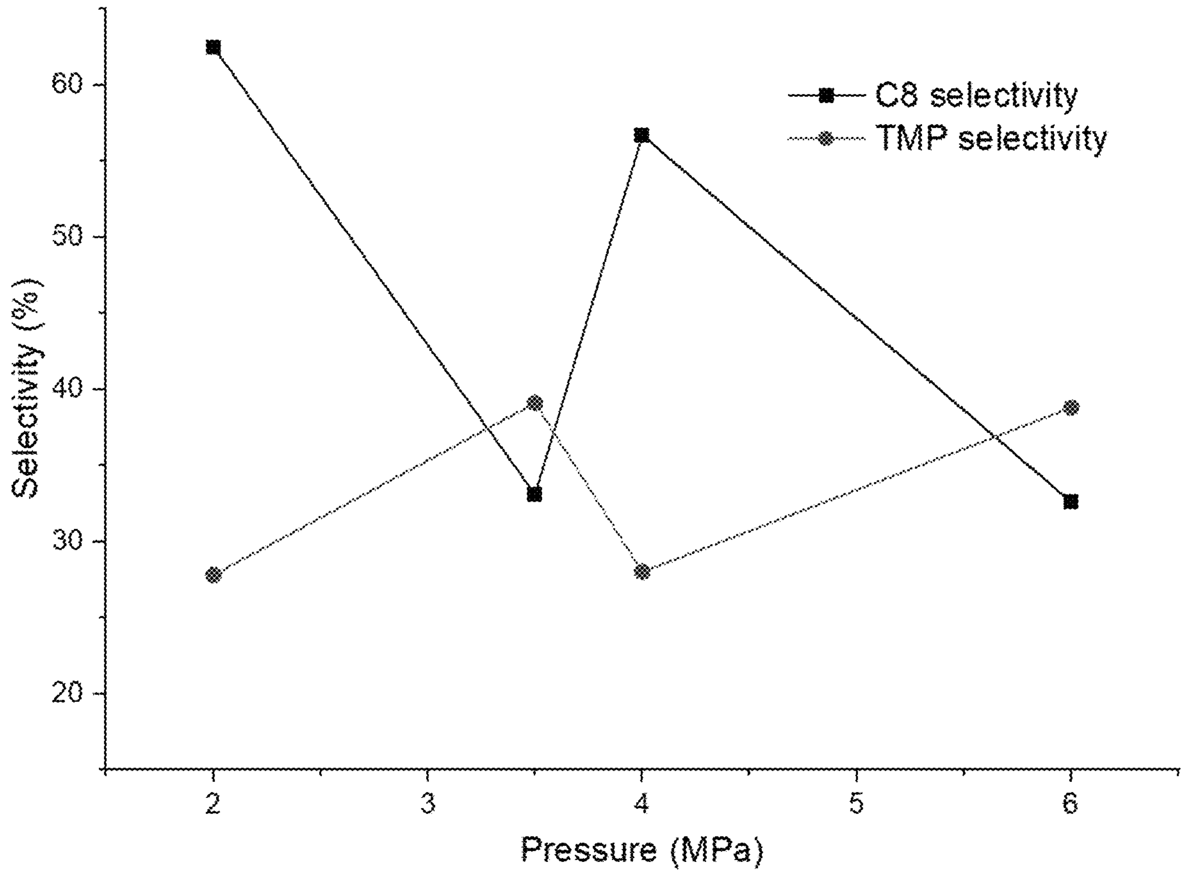
FIG. 6 provides the plot that shows the effect of the reaction pressure on the selectivity towards C8s and TMPs FIG. 7 provides the plot that shows the effect of the reaction pressure on the volume of the produced gasoline and on the TMP/DMH ratio.
Figure 7:
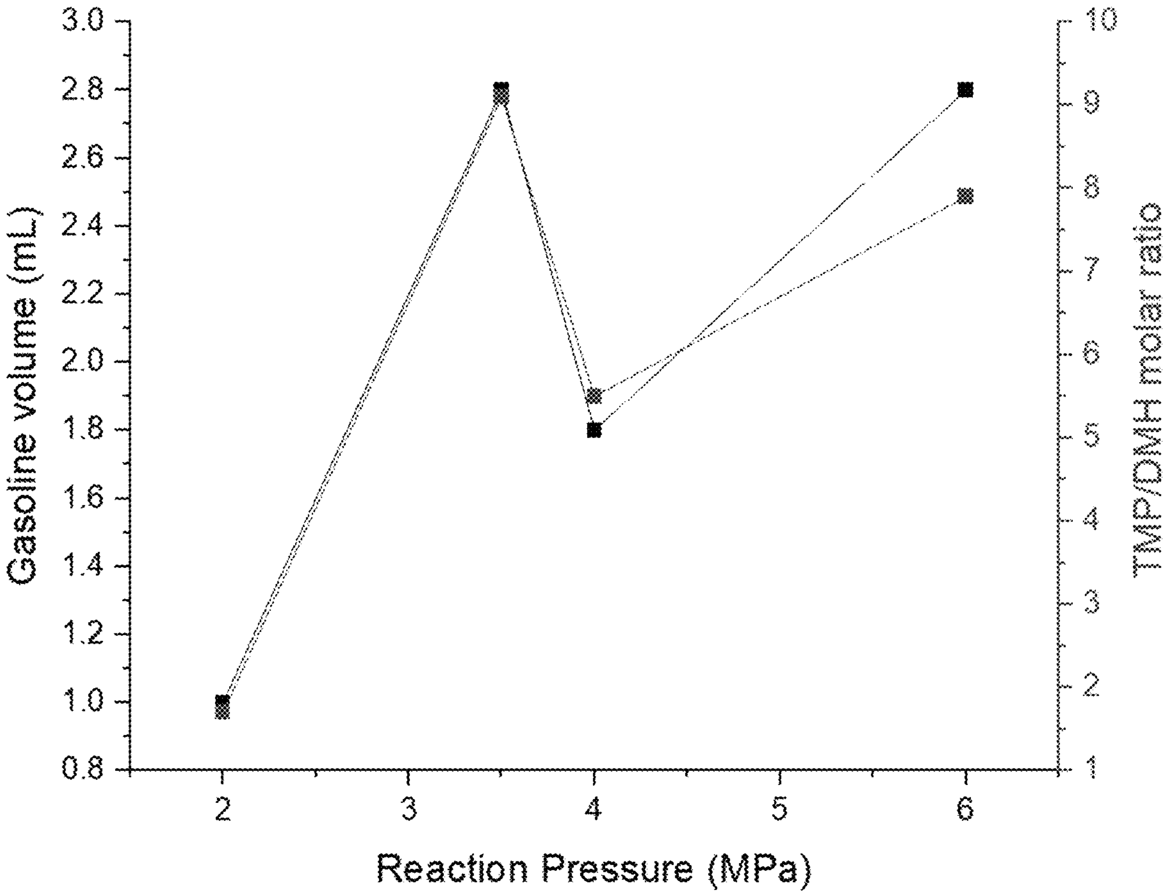

Effect of the reaction pressure. FIG. 6 shows the relationship between the pression of the reaction and the selectivity to C8s and TMPs. The reactions were carried out under the following conditions: Temperature 80° C., time 15 min, HC/MSA ratio of 50 weight %, agitation: 1500 rpm at 2, 3.5, 4 and 6 MPa of pressure. From a practical perspective, the change in pressure did not represent any change in trend, whether to increase or decrease the selectivity, since such parameters erratically changed, showing no trend (see FIG. 6). In practice, it seems favorable to leave a low pressure, which means that no nitrogen was necessary to increase it. Instead, the final pressure of 2 MPa was autogenic. Notwithstanding, FIG. 7 proofs that the increase in pressure favors the yield of the gasoline product (up to 3 mL respective to the used reactants), keeping the TMP/DMH ratio values higher than those obtained using sulfuric acid as catalyst. These results indicate that an increase in pressure leads to a higher yield of products, representing advantages when industrial applications are envisaged.

Figure 8:
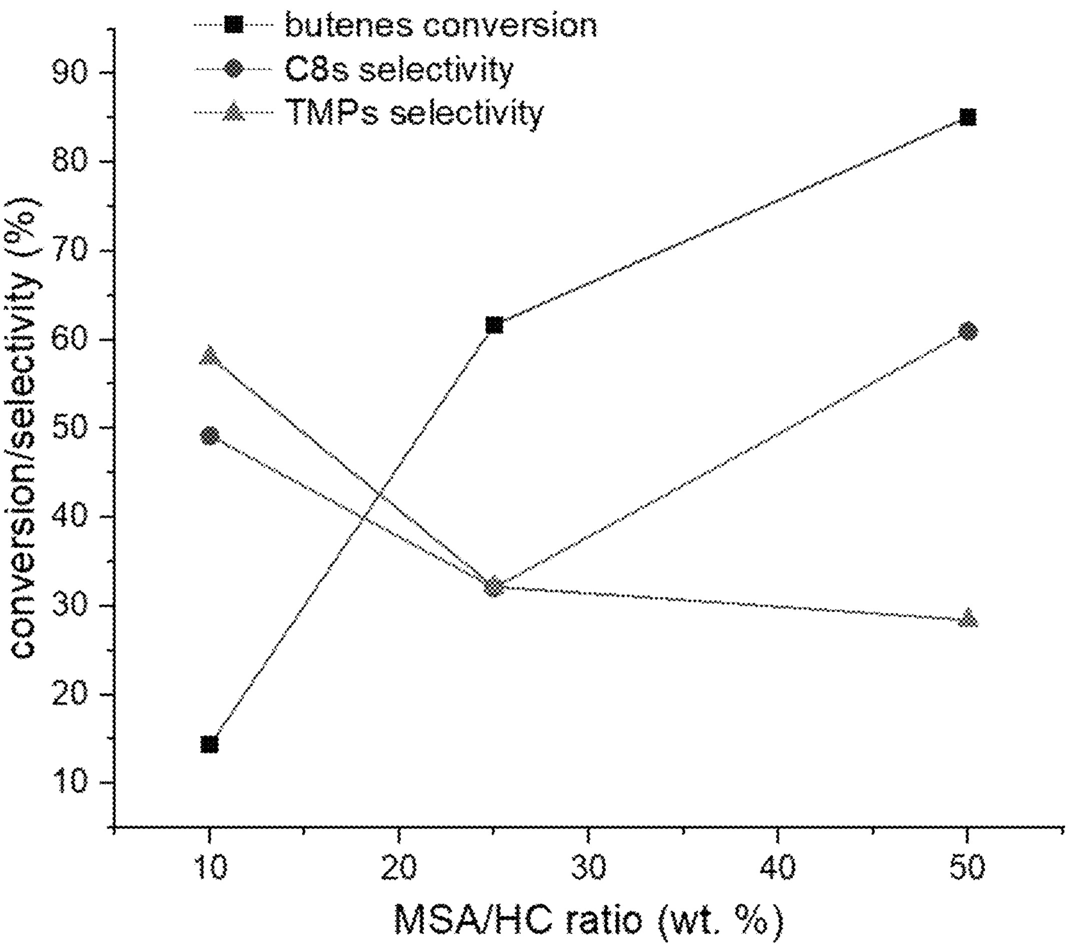
FIG. 8 exhibits the plot showing the reusability of the catalytic process through the values of C8s, C9+ and C5-C7.

Effect of the catalyst/hydrocarbon (cat/HC) weight ratio. FIG. 8 presents the relationship between the weight % of the catalyst and the conversion/selectivity values of the obtained alkylate. The conversion of butenes is notoriously increased when the catalyst mass is also increased, but the selectivity to TMPs is significantly diminished (from 58% to 32.2 and 28.5% at 10, 25 and 50 weight %) and, regarding the selectivity to C8s, this falls at 25 wt. % of catalyst; however, it ends in a value of 60% at 50 weight % of catalyst.

Catalyst reuse. The gasoline production process here described can be boosted by the reuse of the single catalyst, namely, methanesulfonic acid. The reuse process can be described as follows:

Once the reaction time is accomplished, the reactor is vented, at −5° C. by using the scape valves. Later on, the reactor is opened, and the liquid content is decanted to a beaker at 0° C., where the volatiles are allowed to evaporate. Part of the catalyst remaining in the reactor is at the solid phase, which allows to be easily separated from the reaction products by decantation, so it can be used in a subsequent reaction cycle without any previous treatment. It is expected that a fraction of the catalyst is lost during the handling of the reactor, but also it can be lost due to its mixing with the alkylate product. In this case, the amounts of reactants are adjusted to the amount obtained of used catalyst.

Figure 9:
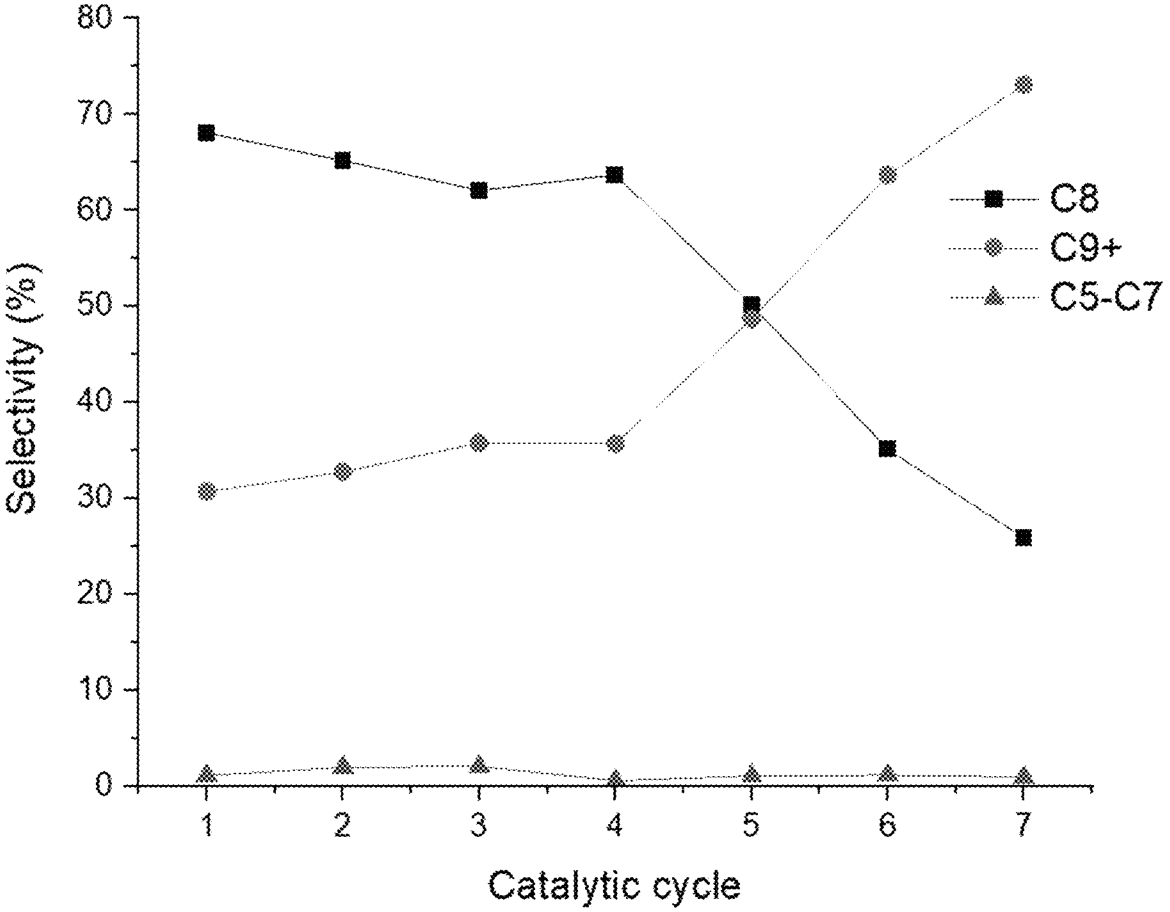
FIG. 9 shows the results of recyclability of the MSA catalyst, undertaken at Batch experiments at 50° C.

FIG. 9 shows the results of recyclability of the MSA catalyst, undertaken at Batch experiments at 50° C. These results reveal a stable catalytic activity for up to 4 reaction cycles, reaching selectivity to C8 higher than 60%. After the 4th reaction cycle, the catalytic activity starts to decay, and the heavy end products (C9+) become more abundant. To note that the amount of hydrocarbons lower than C8 (C5-C7) does not undergo significant modifications, showing that the production of lower ends by cracking reactions is negligible.

The results up to this point shown demonstrate the capacity of MSA to catalyze the alkylation reaction of olefins and iso-paraffins, and its capacity to be recycled in subsequent reaction cycles. The regeneration process shown here is not limited to Batch experiments, but it can be replicated at continuous regime processes, provided that the technical modifications are done.

General considerations of the gasoline production process of this disclosure: Through this gasoline production process, methanesulfonic acid (MSA) is used as the single catalyst for the reaction; this catalyst allows a proper separation from the reaction products, leading to a facile reutilization of the catalyst, which, in other processes such as that catalyzed by sulfuric acid, is more complicated, having to regenerate it with fresh acid to keep a minimum acidity of 90%.

This process describes the production of alkylate gasoline through a batch reaction, where, in the following order, are mixed: methanesulfonic acid, hydrocarbon mixtures coming from an alkylation plant, and nitrogen. These are heated to a certain temperature and stirred for a certain amount of time. Once the reaction time has been accomplished, the mixture is cooled to 5° C. and the alkylation product separated from the catalyst by simple decantation. The catalyst can be regenerated by separating form the reaction effluent (decantation) and re-introduction into the reactor without further pre-treatment.

EXAMPLE

The following example is presented to illustrate the process of production of alkylate gasoline with refinery mixtures and organic acids and should not be considered as a limitation of the technical scope of the present disclosure, but they tend to be informative about the best way to employ methanesulfonic acid as single catalyst and its evaluation in a proper way.

In a batch reactor, provided with an internal Teflon lining, methanesulfonic acid is added in amounts within the range of 10-50 weight % of that of the gas mixture. One the reactor is charged; it is sealed and cooler to −5° C. Then, at this temperature, the gas mixture from refinery is injected by using the micrometric valves; such mixture contains olefins and iso-paraffins. Once the mixture is charged, the reactor is taken to a heating place and heating is started at about 5° C./min heating rate, up to the temperatures oscillating between 0 and 140° C. Once the reaction temperature is reached, nitrogen is injected until the working pressure is reached, which is between 2 and 6 MPa. The stirring is started at 1500 rpm through the reactors propel. The working pressure will slightly change due to the formation of the alkylate gasoline. Once the reaction time has been accomplished (which can go from 5 to 30 min) the stirring is switched off, the temperature is stabilized to the ambient one, and then a gas sample is taken by a valve and collected in a plastic bag. The reactor is then cooled to −5° C. and, at that temperature, it is open to extract the liquid product (gasoline), which is kept at the same temperature in a cool bath, and then allowed to reach ambient temperature. Finally, the alkylate is neutralized with a saturated solution of sodic bicarbonate. One neutral, the produced alkylate is taken to a gas chromatograph to determine the content of TMPs and C8s.

BIBLIOGRAPHICAL REFERENCES

Citation of a reference herein shall not be construed as an admission that such reference is prior art to the present invention. All references cited herein are hereby incorporated by reference in their entirety. Below is a listing of various references cited with respect to this example:

(1) Bp Energy Outlook 2023.
(2) Velázquez, H. D.; Cerón-Camacho, R.; Mosqueira-Mondragón, M. L.; Hernandez-Cortez, J. G.; Montoya de la Fuente, J. A.; Hernández-Pichardo, M. L.; Beltrán-Oviedo, T. A.; Martínez-Palou, R. Recent Progress on Catalyst Technologies for High Quality Gasoline Production. Catalysis Reviews 2022, 0 (0), 1-221. doi.org/10.1080/01614940.2021.2003084.
(3) Fahim, M. A.; Alsahhaf, T. A.; Elkilani, A. Chapter 10-Alkylation. In Fundamentals of Petroleum Refining; Fahim, M. A., Alsahhaf, T. A., Elkilani, A., Eds.; Elsevier: Amsterdam, 2010; pp 263-283. doi.org/10.1016/B978-0-444-52785-1.00010-3.
(4) Díaz Velazquez, H.; Likhanova, N.; Aljammal, N.; Verpoort, F.; Martínez-Palou, R. New Insights into the Progress on the Isobutane/Butene Alkylation Reaction and Related Processes for High-Quality Fuel Production. A Critical Review. Energy Fuels 2020, 34 (12), 15525-15556. doi.org/10.1021/acs.energyfuels.0c02962.
(5) Hommeltoft, S. I.; Topsoe, H. F. A. Alkylation Process. U.S. Pat. No. 5,220,095A, Jun. 15, 1993. patents.google-.com/patent/US5220095A/en (accessed 2023 Jan. 5).
(6) Balasubramanian, S.; Venkatachalam, P. Green Synthesis of Carbon Solid Acid Catalysts Using Methane Sulfonic Acid and Its Application in the Conversion of Cellulose to Platform Chemicals. Cellulose 2022, 29 (3), 1509-1526. doi.org/10.1007/s10570-022-04419-7.
(7) Leleti, R. R.; Hu, B.; Prashad, M.; Repič, O. Highly Selective Methanesulfonic Acid-Catalyzed 1,3-Isomerization of Allylic Alcohols. Tetrahedron Letters 2007, 48 (48), 8505-8507. doi.org/10.1016/j.tetlet.2007.09.156.
(8) Luong, B. X.; Petre, A. L.; Hoelderich, W. F.; Commarieu, A.; Laffitte, J.-A.; Espeillac, M.; Souchet, J.-C. Use of Methanesulfonic Acid as Catalyst for the Production of Linear Alkylbenzenes. Journal of Catalysis 2004, 226 (2), 301-307. doi.org/10.1016/j.jcat.2004.05.025.
(9) Chang, Q.; Qu, H.; Qin, W.; Liu, L.; Chen, Z. Methylsulfonic Acid Adsorbed on Silica Gel as a Solid Acid for Dimerization of Indoles: A Convenient Synthesis of 2,3'-Bi (3H-Indol)-3-One Oximes. Synthetic Communications 2013, 43 (21), 2926-2935. doi.org/10.1080/00397911.2012.751611.
(10) Góra, M.; Kozik, B.; Jamroży, K.; Łuczyński, M. K.; Brzuzan, P.; Woźny, M. Solvent-Free Condensations of Ketones with Malononitrile Catalysed by Methanesulfonic Acid/Morpholine System. Green Chem. 2009, 11 (6), 863-867. doi.org/10.1039/B820901D.
(11) Zhang, T.; Li, X.; Dong, J. Methanesulfonic Acid as a More Efficient Catalyst for the Synthesis of Lauraldehyde Glycerol Acetal. Tenside Surfactants Detergents 2014, 51 (6), 516-520. doi.org/10.3139/113.110337.
(12) Kore, R.; Scurto, A. M.; Shiflett, M. B. Review of Isobutane Alkylation Technology Using Ionic Liquid-Based Catalysts—Where Do We Stand? Ind. Eng. Chem. Res. 2020, 59 (36), 15811-15838. doi.org/10.1021/acs.iecr.0c03418.
(13) Gan, P.; Tang, S. Research Progress in Ionic Liquids Catalyzed Isobutane/Butene Alkylation. Chinese Journal of Chemical Engineering 2016, 24 (11), 1497-1504. doi.org/10.1016/j.cjche.2016.03.005.
(14) Campisciano, V.; Giacalone, F.; Gruttadauria, M. Supported Ionic Liquids: A Versatile and Useful Class of Materials. The Chemical Record 2017, 17 (10), 918-938. doi.org/10.1002/tcr.201700005.
(15) Singhal, S.; Agarwal, S.; Singh, M.; Rana, S.; Arora, S.; Singhal, N. Ionic Liquids: Green Catalysts for Alkene-Isoalkane Alkylation. Journal of Molecular Liquids 2019, 285, 299-313. doi.org/10.1016/j.molliq.2019.03.145.
(16) Eastman, A. D. Alkylation Catalyst Regeneration. US005284993A, Feb. 8, 1993.
(17) Abbott, R. G. Isoparaffin-Olefin Alkylation Catalyst Composition and Process. U.S. Pat. No. 5,292,986A, Mar. 8, 1994. patents.google.com/patent/US5292986A/en (accessed 2023 Jun. 16).
(18) Xuang, M.; Li, S. Gasoline Desulfurization by Catalytic Alkylation over Methanesulfonic Acid. Bull. Kor. Chem. Soc. 2013, 34 (10). doi.org/10.5012/bkcs.2013.34.10.3055.
(19) Tian, Y.; Meng, X.; Duan, J.; Shi, L. A Novel Application of Methanesulfonic Acid as Catalyst for the Alkylation of Olefins with Aromatics. Ind. Eng. Chem. Res. 2012, 51 (42), 13627-13631. doi.org/10.1021/ie302015v.
(20) Zhao, Z.; Li, Z.; Qiao, W.; Wang, G.; Cheng, L. An Efficient Method for the Alkylation of α-Methylnaphthalene with Various Alkylating Agents Using Methanesulfonic Acid as Novel Catalysts and Solvents. Catal Lett 2005, 102 (3), 219-222. doi.org/10.1007/s10562-005-5859-1.
(21) Luong, B. X.; Petre, A. L.; Hoelderich, W. F.; Commarieu, A.; Laffitte, J.-A.; Espeillac, M.; Souchet, J.-C. Use of Methanesulfonic Acid as Catalyst for the Production of Linear Alkylbenzenes. Journal of Catalysis 2004, 226 (2), 301-307. doi.org/10.1016/j.jcat.2004.05.025.

The invention claimed is:

1. A process for production of alkylate gasoline using a refinery mixture containing olefins and iso-paraffins, said process comprising:

(a) adding an organic acid catalyst comprising methanesulfonic acid at 99% purity in amounts ranging from 10 to 50 weight % respective to the mass of the refinery mixture and the organic acid, to a batch reactor provided with a Teflon lining and a propeller;

(b) sealing and cooling the reactor to −5° C.;

(c) adding the refinery mixture containing olefins and iso-paraffins, by the employment of micrometric valves;

(d) connecting the reactor to a heating device and heating at a rate of 5° C./minute up to a temperature within a range of 0 to 140° C.;

(e) injecting nitrogen to pressures within a range of 2 to 6 MPa and, at the same time, stirring the reaction at 1500 rpm using the propeller for reaction times from 5 to 30 minutes;

(f) shutting off heating and stirring;

(g) stabilizing the product mixture to ambient temperature;

(h) taking a gas sample by using a gas collector plastic bag;

(i) afterwards, cooling down the reactor to −5° C.;

(j) extracting a liquid product comprising alkylate gasoline at −5° C. and a solid used catalyst;

(k) neutralizing the liquid product comprising alkylate gasoline with a saturated solution of sodium bicarbonate at ambient temperature; and (l) recycling the solid used catalyst in consecutive production of alkylate gasoline according to steps (a)-(k).

2. The process according to claim 1, wherein the solid used catalyst is recovered from the reactor without any prior treatment.

3. A solid methanesulfonic acid catalyst produced according to the process of claim 2.

4. A method comprising using the solid methanesulfonic acid catalyst according to claim 3, wherein the catalyst is used in up to 4 consecutive reaction cycles without any detrimental effects on the catalytic activity of the catalyst.

5. The method according to claim 4, wherein in each of the consecutive reaction cycles, the weight ratio of the solid used catalyst to the refinery mixture is 50 weight %, and stirring is at 1500 rpm.

* * * * *